United States Patent [19]

Schiller et al.

[11] Patent Number: 5,195,115
[45] Date of Patent: Mar. 16, 1993

[54] X-RAY DIFFRACTOMETER DEVICE AND USE OF THIS DEVICE

[75] Inventors: Claude Schiller, Savigny-Sur-Orge; Jean-Pierre Weber, Saint-Maur, both of France

[73] Assignee: U.S. Philips Corp., New York, N.Y.

[21] Appl. No.: 733,925

[22] Filed: Jul. 22, 1991

[30] Foreign Application Priority Data

Jul. 24, 1990 [FR] France ................ 90 09443

[51] Int. Cl.$^5$ ............................. G01N 23/207
[52] U.S. Cl. ............................. 378/73; 379/79; 379/158
[58] Field of Search .............. 378/73, 71, 79, 81, 378/145, 156, 157, 158

[56] References Cited

U.S. PATENT DOCUMENTS

| 3,030,512 | 4/1962 | Harker | 378/157 |
|---|---|---|---|
| 5,003,569 | 3/1991 | Okada et al. | 378/71 |

Primary Examiner—David P. Porta
Attorney, Agent, or Firm—William L. Botjer

[57] ABSTRACT

The invention relates to an X-ray diffractometer device, comprising an X-ray source, a collimator device for the source, a sample support, a collimator device for the beam reflected by the sample and a counter producing an output signal in the form of a voltage which is proportional to the number of photons reflected by the sample. This device furthermore includes a motor drive for the sample support, recording means for the signal Y originating from the proportional counter as a function of the angle $\theta$ between the plane of incidence of the sample and the incident beam, denoted X, mechanical means having a support for a plurality of filters having different coefficients of absorption and including a motor drive for this filter support, data processing means for selecting one of the filters of the filter support and for controlling the motor drive of the sample support, the motor drive of the filter support and the recording means, respectively.

10 Claims, 5 Drawing Sheets

X-RAY DIFFRACTOMETER DEVICE AND USE OF THIS DEVICE

FIELD OF THE INVENTION

The invention relates to an X-ray diffractometer device, comprising an X-ray source, a collimator device for the source, a sample support, a collimator device for the beam reflected by the sample and a counter producing an output signal in the form of a voltage which is proportional to the number of photons reflected by the sample.

The invention also relates to the use of this glancing device in the slanting incidence mode.

The invention is used in the characterization of multi-layer structures utilized in the X-ray technique, such as, for example, multi-layer mirrors for X-ray optical devices, as well as for measuring the widths of layers of metal, semiconducting or insulating materials having different optical indices.

Thus, the invention allows the measurement of the widths of layers in the nanometer range, the measurement of these widths when two or three nanometer layers of different materials are stacked (two- or three-layer systems), the measurement of the pitch with which the stacking is repeated, the measurement of characteristic parameters of the materials forming these layers, and consequently the identification of these materials, the determination of the surface roughness or the average roughness of the stack.

BACKGROUND OF THE INVENTION

An X-ray diffractometer device is already known from the prior art apparatus, type designation PW1050, marketed by Messrs. PHILIPS (I α E ANALYTICAL ALMELO, the Netherlands).

This device comprises an X-ray source, a system of collimation slits for the beam coming from the source, a sample support, arranged such that the incident beam reaches the sample at an angle of incidence equal to $(\pi/2) - \theta$, or, put differently: at an angle $\theta$ to the plane of the sample-support, a collimation slit system of the reflected beam, and a detector for detecting the number of reflected photons, of the proportional counter type.

Proportional counter must here be understood to mean a device containing gas which can be ionized by the flux of photons to be detected and supplies a signal in the form of a voltage which is proportional to the number of photons. Actually, the response of the proportional counter is only linear in a certain range of intensities. When the intensities reflected by the sample are too weak or too strong, one lands outside the linearity region of the counter.

Now, the diffractometry device already commercially available is not suitable for the intended use to characterize multi-layer samples, and also not for measuring layer widths, because of the fact that it can only operate in a certain range of angles of incidence. Thus, this apparatus is perfectly suitable for measuring mesh parameters of samples of powders of different materials, since in the case of powders, the angles of incidence do not have very high values, that is to say they are generally not located in the range of glancing angles or orthogonal incidences. The measurement of the mesh parameters is obtained by interpreting variations in the output signal of the proportional counter. These variations form peaks having an amplitude which is proportional to the number of photons received by the detector and whose distance is also characteristic of the material, more specifically of its mesh parameters. Comparing these measurements to the data contained in Classifying Tables renders it possible to determine the mesh parameters of the powder under investigation and to derive therefrom the nature of the composite material.

Measuring the mesh parameters by means of this method, using the known apparatus with the type designation mentioned in the foregoing, is founded on the Bragg relation:

$$2d \cdot \sin \theta = \lambda,$$

wherein $\lambda =$ the wavelength of the source, constant value, $\theta =$ the angle between the path of the incident beam and a reticular plane of the investiagted material, $d =$ the mesh parameter of the material forming the investigated powder, for example.

As the prior art apparatus is arranged for investigating powders, in conditions far removed from glancing incidence, the measurements performed with this apparatus can only be applied to materials having a mesh parameter d of a low value.

Now, at present it is necessary that one can characterize not only powders, but also bulky elements, for example multi-layer mirrors operating in the field of soft X rays, or thin metal, semiconducting or insulating layers, all solid materials.

For example, the said bulky element or multilayer mirror is formed by an alternation of at least two materials having different indices of refraction: a what is called heavy material and a what is called light material. The spacing between the layers is imposed by the structure of the mirror.

Characterizing this type of bulky element requires the measurement of large parameters d. Consequently, from the relation stated hereinbefore, the result is that, the wavelength of the source being fixed, only the measurement at very small angles of incidence $\theta$ (glancing incidence) renders it possible to obtain the characterization of materials having large parameters d, or, when layer thicknesses are measured, allows measuring of widths comprised between 1 and 300 nm.

It is not possible with the known apparatus, whose type designation has been mentioned hereinbefore, to operate in the case of very glancing incidence because of limitations of the proportional counter. In fact, with glancing incidence, the reflected intensities are very strong, and because of a saturation phenomenon, the proportional counter is outside the range of intensities in which its response is linear. Consequently, it is not possible to obtain the characterization of the intended samples, mentioned in the foregoing, using the known apparatus.

On the other hand, for solid samples such as the said multi-layer mirrors, it must be necessary that the angle of incidence $(\pi/2) - \theta$ of the values wherein $\theta = 0$ to the values wherein $\theta$ is still low but not zero, for example $\theta = 2°$ or $\theta = 4°$. During this variation, the reflected intensity varies in large proportions. If, for example, the reflected intensity is within the linearity range of the proportional counter for $\theta = 0°$, it is no longer in this range, by lack of intensity for $\theta = 2°$. Conversely, if the intensity is within the linearity range of the proportional counter for $\theta = 2°$, it is no longer in this range for $\theta = 0°$ because of the excessive increase of the reflected intensity.

A solution known to a person skilled in the art of optics of the problem created by an excessively high luminous intensity in a system, is to interpose an absorbing filter.

But, as has been stated in the foregoing, this solution is not directly applicable to the prior art apparatus, because of the fact that if the reflected intensity is within the linearity range of the counter in one of the measuring conditions, it is no longer in this range from the instant at which the conditions for the same measurement have changed.

A solution must therefore be found for the problem of interposing a given filter as a function of the photonic intensity reflected from a given sample when the measuring conditions vary during one measurement.

The solution then found renders it possible to realise measurements not only of solid samples but also of samples with large mesh parameters, as well as of samples which are simultaneously solid and have large parameters, that is to say when the parameters of the sample vary from one measurement to the other.

SUMMARY OF THE INVENTION

According to the invention, this problem is solved using a device having characteristics as defined in the opening paragraph and furthermore having characteristics defined in the characterizing part of the claim 1.

Such a device has the advantage that, as soon as the reflected intensity approaches a value from which the proportional counter does not operate linearly anymore, the absorbing filter, when active, is automatically replaced by a different filter whose absorption is such that the proportional counter again operates linearly.

Thus, on the one hand the proportional counter always operates in the range in which it is linear, and on the other hand all the measurements can be effected continuously, whatever the angle and/or type of sample, without the need for action on the part of the operator.

BRIEF DESCRIPTION OF THE DRAWINGS

The invention and its advantages will be better understood from the following description given with reference to the accompanying Figures:

FIG. 2b is a schematic view of the mechanical portion of this system taken on the line III—III of FIG. 2a;

Figure 1:
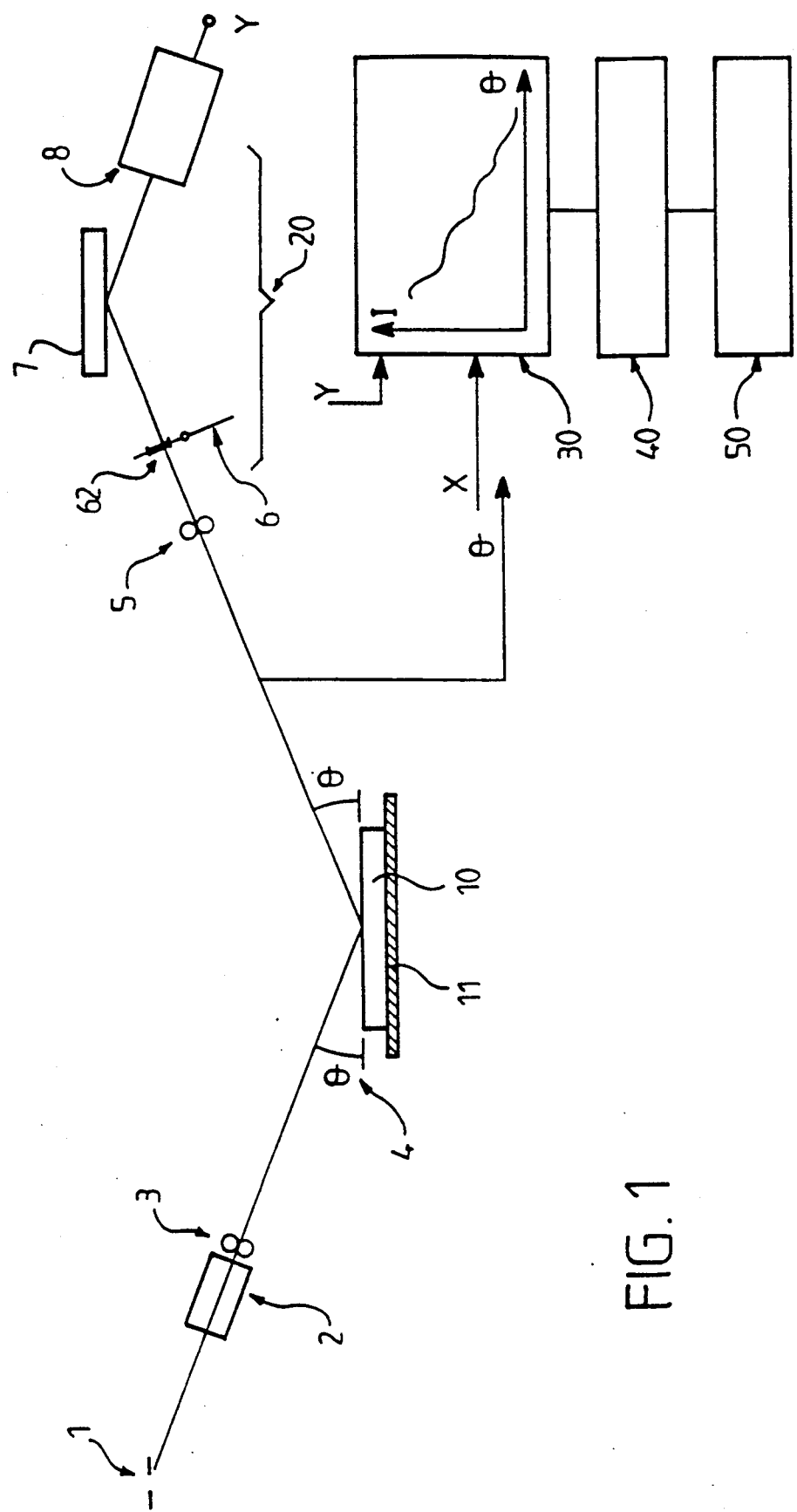
FIG. 1 is a schematic view of a standard diffractometer device, additionally provided with a measurement automation system in accordance with the invention.

As is shown in FIG. 1, an X-ray diffractometer apparatus includes at least the elements known from the commercially available Philips apparatus PW1050, i.e.

a linear X-ray source 1 ; actually, the X-ray sources available on the market have a linear source this source is furthermore positioned such with respect to the optical axis of the device that it encloses with this axis a smaller or a wider angle, denoted sampling angle ; the useable luminous intensity may depend on the sample angle;

a collimator system 2 and 3 including the Soller slits 2 and a divergence slit 3;

a goniometric sample support 11 comprising sample orientation means 10, not shown; these orientation means comprise more specifically the control of the angle of incidence; for the sake of simplicity, the expression "incidence $\theta$" will be used to designate the angle $\theta$ between the beam and the sample plane when the angle of incidence is $(\pi/2)-\theta$;

a collimator system 5 formed by a so-called receiving slit;

a monochromator 7 of the graphite monochromator type, in the field of XR (X-rays);

a proportional counter 8.

DESCRIPTION OF THE PREFERRED EMBODIMENTS

In accordance with the invention, the prior art apparatus is modified to render the measurement of large parameters d possible, the value d of predetermined parameters being linked to $\theta$ and $\lambda$, the wavelength of the source by the relation 2d Sin $\theta = \lambda$, the so-called Bragg relation.

On the one hand, to obtain the measurement of ever larger parameters d, the choice of the source is influenced, that is to say the choice of $\lambda$. To this effect the X-ray source is chosen from among one of the sources specified in Table I which shows the wavelengths $\lambda$ in $\text{Å} = (1/10)$nm as a function of the rays K$\alpha$ of several X-ray metal sources.

On the other hand, one opts for having the angle $\theta$ vary in the range in which the incidence is a glancing incidence, i.e. for $0° \leq \theta 2°$ of angle This modified apparatus is used in the determination of the mesh parameters of solid materials, the width of mulyi-layer materials such as interferential mirrors for X rays, surface roughness values or average stack roughness values.

When the apparatus operates in the glancing incidence mode, the intensity reflected by a solid sample 10, located on the sample support 11, is much greater than when the sample is a powder.

For a flat sample, the reflection of the beam is total, i.e. the reflectivity is equal to 1, up to an angle $\theta_c$ which more specifically depends on the wavelength $\lambda$, the density and the nature of the material.

The result is that the proportional counter 8 receives a quantity of photons which is greater than provided by the designer and the counter then is in a non-linear operating range.

To resolve this problem, in accordance with the invention, there is inserted in the path of the beam reflected by the sample, between the receiving slit 5 and the graphite monochromator 7, an appropriate filter 62, for absorbing a portion of the reflected intensity in such a manner that the intensity of the baem propagating towards the porportional counter 8 corresponds to a linear operating range of this counter.

In addition, when in order to perform the measurements, one causes the angle of incidence to vary, for example between 0 and 2°, the reflected intensity varies. As a function of the material, the reflected intensity can decrease in a certain range of variation of the angle $\theta$, evidence peaks for certain values of $\theta$, the amplitude of the peaks and the position of the peaks being characteristics of the material which characteristics allow the determination of the parameters mentioned hereinbefore with reference to the Classifying Tables.

To enable the continual use of the proportional counter 8 in a linear operating range whatever the angle of incidence $\theta$ and consequently the value of the reflected intensity, means 6 are provided in accordance with the invention with the object of inserting a plurality of filters 62, for example 62a, 62b etc. between the receiving slit 5 and the graphite monochromator 7. The absorption of these filters is chosen as a function of the reflected intensity to provide that the proportional counter 8 always operates in a linear operating range.

The Table I shows as a function of the X-ray sources and their associated wavelength $\lambda$ (in Å), examples of filters made of different metals (Ni, Al, Cu) having widths e in $\mu m$ to obtain the absorption coefficients $A = I_0/I$, $I_0$ being the incident intensity, and I the intensity after absorption by the filter.

In the Table I the filter widths e are given, as well as the metals from which the filters are made, in such a manner that absorption coefficients A are obtained which are as close to the value 10 as possible; examples of filters are also given (width e, and metal material) to obtain an absorption A as close as possible to 5. Other values of the absorption A may be chosen by a person skilled in the art by interpolating values on the basis of Table I. For example, absorption coefficients A are obtained having the respective values $10^0, 10^1, \ldots 10^n$ (wherein n is an integer) by multiplying the widths e from $e=0$ (corresponding to $A=1$) up to nxe when e corresponds to an ansorption coefficient of approximately 10.

In accordance with the invention, an automation system is thereafter provided for positioning the appropriate filter 62 to ensure that the proportional counter continually operates in a linear operating range whatever the angle of incidence $\theta$.

The automation system 20 includes mechanical means 6 to support the filters and to position them and data processing means for controlling the filter supports.

In accordance with the invention, there is further provided a system 30, 40, 50 for processing the signal Y coming from the proportional counter as a function of the information X formed by the incidence $\theta$, to obtain a curve Y as a function of continuous X by associating the curve section obtained in the various intensity regions covered during a measurement, and to obtain a systematic comparason to theoretical curves so as to automatically effect the determination of the envisaged parameters.

FIG. 1 shows, in addition to the automation device 20, the display screen 30 on which the curves of the intensities I appear as a function of the angle $\theta$; the data processing computer is denoted by reference numeral 40; and the block 50 represents the theoretical curves obtained on the computer.

Figure 2A:
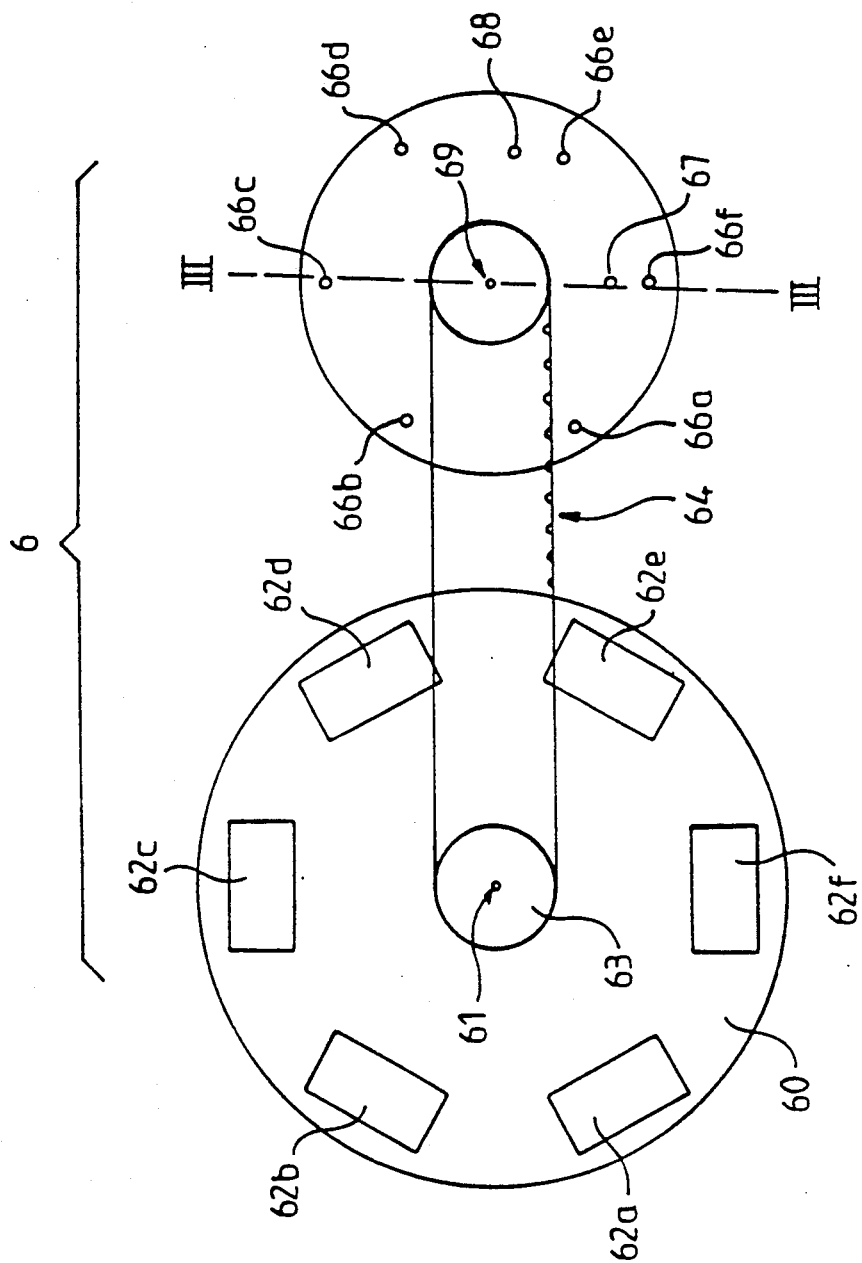
FIG. 2a is a schematic view of the mechanical portion of this automation system in a plan view.

FIG. 2a is a front view, i.e. a view perpendicularly to the plane of FIG. 1, of mechanical means 6 for supporting the filters and putting them in position.

TABLE I

| Source | λ(source)Å | Metal(filter) | e(filter)μm | A |
|---|---|---|---|---|
| Mo Kα | 0.709 | Ni | 50 | 8.2 |
| Cu Kα | 1.542 | Ni | 50 | 9 |
| Ni Kα | 1.659 | Ni | 50 | 14.3 |
| Ni Kα | 1.659 | Al | 100 | 5.4 |

TABLE I-continued

| Source | λ(source)Å | Metal(filter) | e(filter)μm | A |
|---|---|---|---|---|
| Ni Kα | 1.659 | Al | 140 | 10.0 |
| Co Kα | 1.790 | Al | 100 | 8.11 |
| Fe Kα | 1.937 | Al | 60 | 5 |
| Fe Kα | 1.937 | Al | 90 | 10.8 |
| Cr Kα | 2.290 | Al | 60 | 12.93 |
| Cr Kα | 2.290 | A | 45 | 6.8 |
| | | ρ(Ni) = 8,90 | | |
| | | ρ(Al) = 2,70 | | |

TABLE II

| Source | λ(source)Å | Metal (filter) | No (filter) | e(filter)μm | A |
|---|---|---|---|---|---|
| Ni Kα | 1.659 | Al | 62 e | 140 | 10 |
| | | | 62 d | 2 × 140 | $10^2$ |
| | | | 62 c | 3 × 140 | $10^3$ |
| | | | 62 b | 4 × 140 | $10^4$ |
| | | | 62 a | 5 × 140 | $10^5$ |
| | | | 62 f | 0 | 1 |

These mechanical means 6 comprise a filter support 60 having N windows, to accomodate N filters. When $N=6$ as is shown in FIG. 2a, the filters have reference numerals 62a, 62b, 62c, 62f and 62e. They are arranged such that, when one passes in a continuous manner from one filter to the other, they have an absorption with decreases by a constant factor.

In the specific case represented by way of example in FIG. 2a, a filter support 60 in the shape of a round plate is chosen which can rotate around its axis 61. The filters are accomodated in equally spaced peripheral apertures. The value of the absorption coefficients A of the filters is chosen such that it decreases by a factor closest possible to 10 when one passes from one filter to the other.

Thus, using Table I, it is possible to realise the automation device shown in FIG. 2a, while chosing, for example, the different filters of the Table II, for, for example, a NiK $\alpha$ source.

In order to bring a given filter 62 into the path of an X-ray beam reflected by the sample 10, the plate 60 rotates around its axis 61 under the action of a transmission belt 64 connected to a second plate 68. This plate 68 is driven, for example via its shaft 69, or via any other means, simultaneously with the plate 60, by a first motor, denoted "filter motor". The second plate 68 includes apertures 66a to 66e equal to the number of filters 62a to 62f, uniformly distributed around its circumference.

Figure 2B:
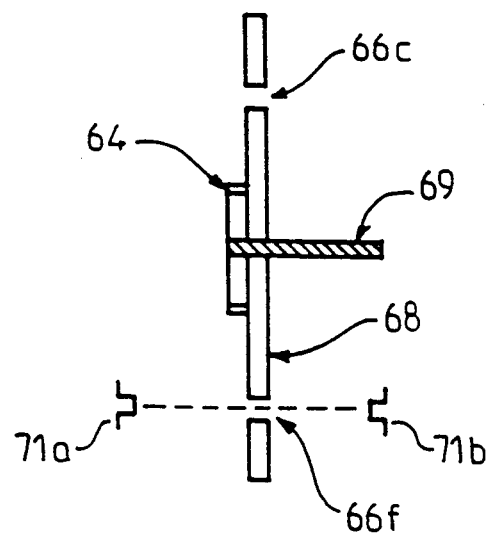

FIG. 2b is a sectional view along the axis III—III of FIG. 2a. So as to position a given filter in the path of the beam reflected by the sample 10, two emitter-receiver diodes 71a, 71b are arranged on either side of the plate 68, at a distance from the axis 69 equal to the distance of the apertures 66. The apertures 66 are posioned such that when a filter is in the chosen position, an aperture 66 is simultaneously located in the axis of the emitter-receiver diodes 71a–71b, so that the signal from the receiver diode controls stopping of the "filter motor" driving the plates 60 and 68.

The "filter motor" which simultaneously drives the positioning control plate 68 and the filter support plate 60 is moreover controlled by data processing means. The object to be achieved by the device in accordance with the invention is to obtain the continuous recording of the signal supplied by the proportional counter as a function of the incidence $\theta = X$.

Figure 3:
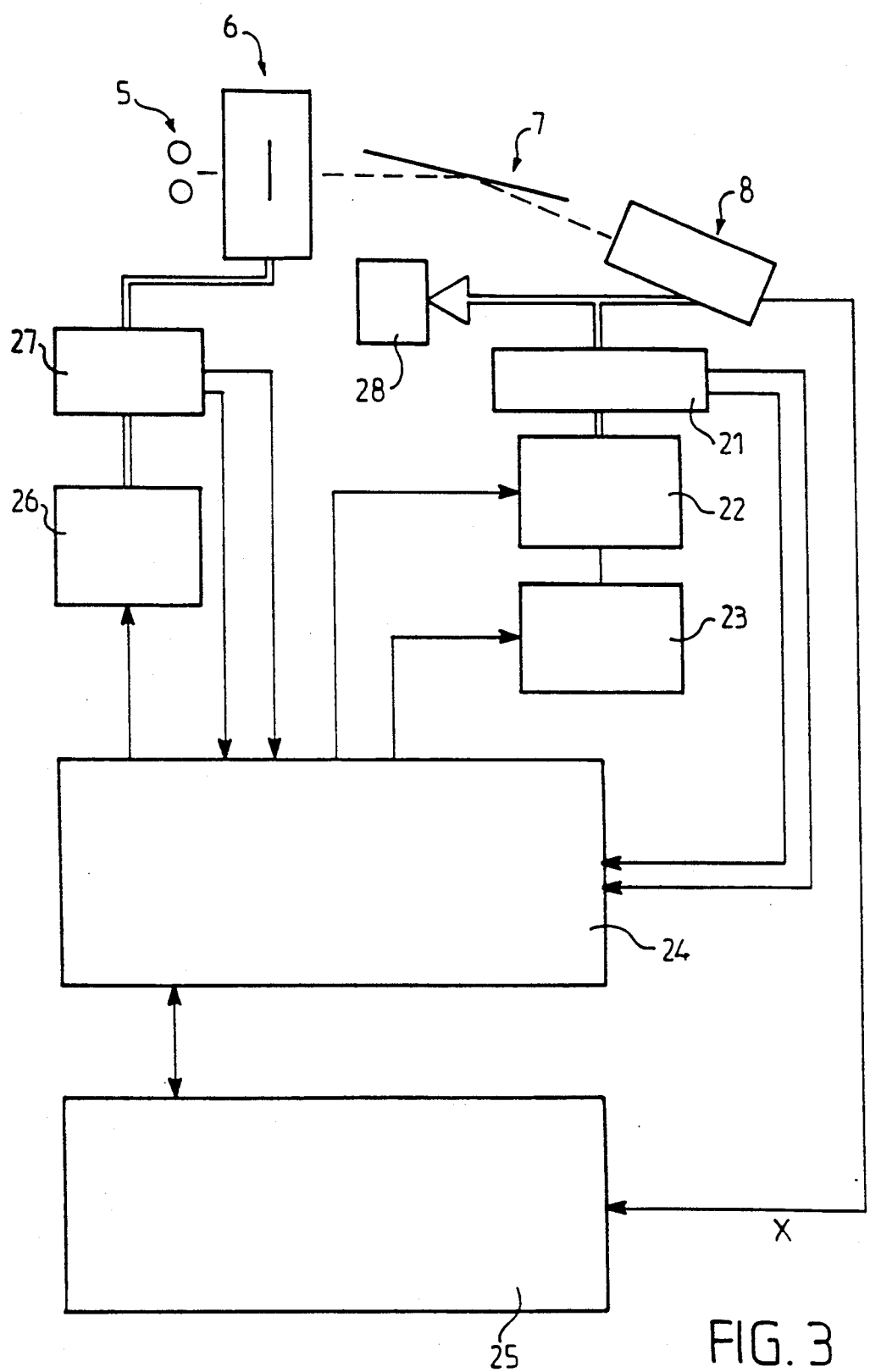
FIG. 3 illustrates, by means of a block diagram, the processing procedure of the measuring signal in the automation system.

The functions put into effect by the control processing means are shown in FIG. 3.

These functions include encoding, by means of an encoder 27, of a signal corresponding to the filter located in the path of the reflected beam. This encoded information is then transferred as data to a microprocessor card 25 in combination with a main computer 25.

The function of starting (start-stop) the first motor, called "filter motor", is denoted 26. On the other hand, the signal Y provided by the proportional counter 8 is recorded in mV as a function of $\theta$, (signal X). As soon as the signal X gets either less than a predetermined value, or higher than an other predetermined value, the stop order for a second motor, called "sample motor", which causes the sample to proceed by one step $\Delta\theta$ when there is incidence $\theta + \Delta\theta$, is given to the microprocessor card 24, via an encoder 21. The order to stop reaches the "sample motor" 28 via the start-stop function 22, via the encoder 21.

The "filter motor" 26 then starts operating to allow, via the system 6, the positioning of either a more absorbing or less absorbing filter. This operation is effected by the control 26 of the "filter motor" which reaches the system via the encoder 27.

Once the rotation of the filter support 60 has been realised, the "filter motor" is stopped (by the diode system 71a–71b) and the command to restart the recording is given by the start-stop control 22 of the "sample motor" via the encoder 21. On the other hand, the function 23 is a function to reverse the "sample motor" when the said motor arrives at the end of run 0 or $\theta$ in one direction or the other.

When the least absorbing filter is in position (for example the filter 62f, having absorption 1), recording of the data Y coming from the counter and X coming from the sample motor might continue without cessation, even if the measured value becomes low at a predetermined low limit value.

The encoder 21 located on the sample motor allows in essence the choice of the measuring steps $\Delta\theta 0$.

In these, using the device in accordance with the invention, an extension of the counting rate of the proportional counter is obtained.

Figure 4A:
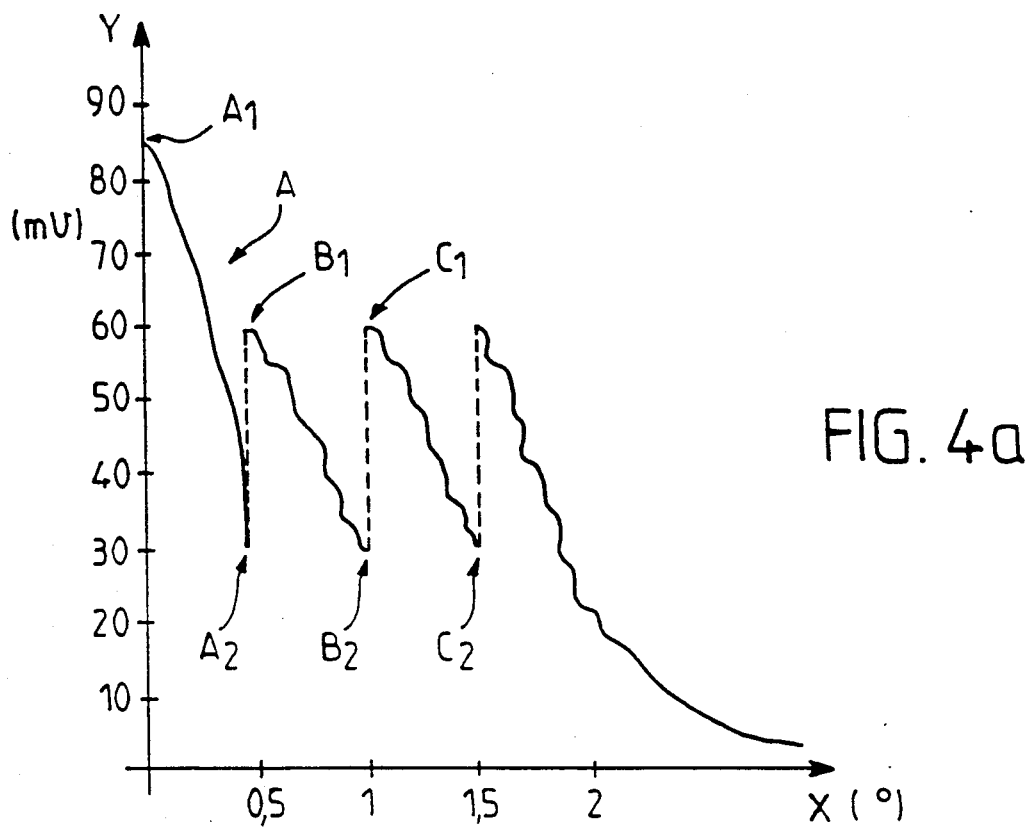
FIG. 4a shows an example of a measurement obtained with the aid of the diffractometry device provided with the automation system, before digital processing.

FIG. 4a shows an irregular curve obtained by means of the device in accordance with the invention. In the portion A of the curve, the reflected intensity, plotted at Y, is first very great. Therefore a highly absorbing filter is used. Thereafter the intensity decreases as a function of the angle $\theta$ plotted at the X axis. In the bottom region of the portion A, this intensity will be difficult to define if the recording is not cut off at point $A_2$. The highly absorbing filter is then replaced by a filter which is approximately 10 times less absorbing, by rotating the filter support 60, the recording is thereafter restarted. Then the portion $B_1 - B_2$ is obtained. At $B_2$, the intensity becomes still weaker and recording is again stopped. The filter is replaced by a filter approximately 10 times less absorbing, by rotating the filter support 60, the recording is thereafter restarted.

If in contrast thereto, the intensity increases to beyond a predetermined value, the recording is again stopped and a filter having a higher absorption is brought into position.

Thus, positioning of the filter appropriate to the predetermined intensity range is effected automatically. There is no need for the operator to interfere in this operation during the course of recording of the signal Y of the counter as a function of $X = \theta$.

Figure 4B:
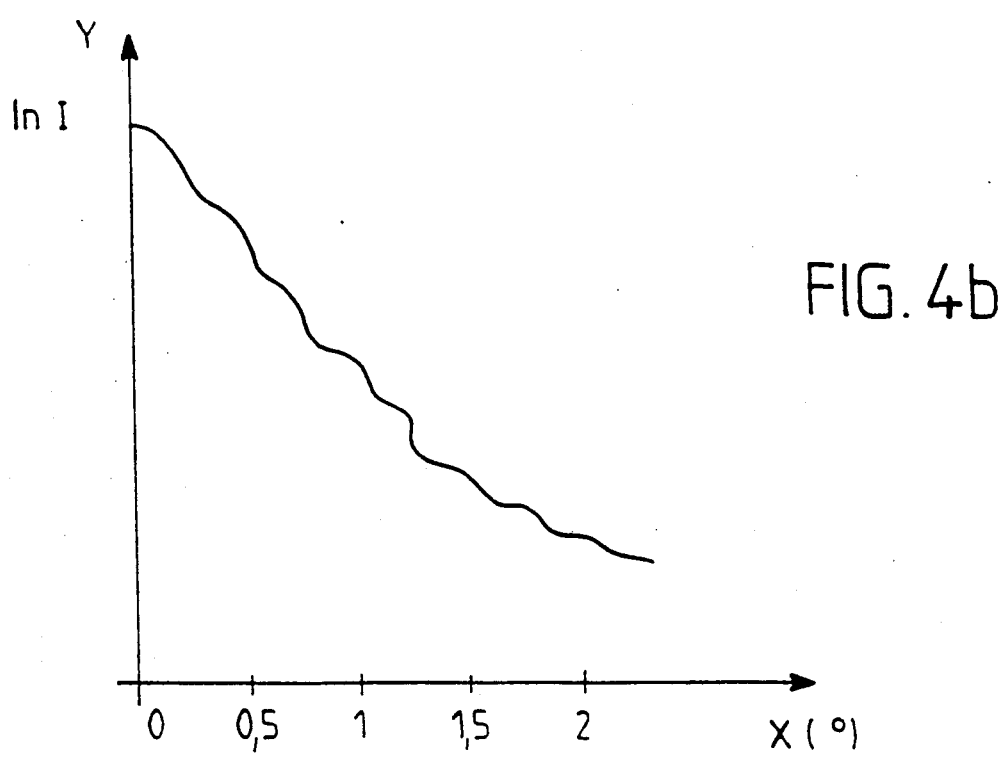
FIG. 4b shows the same example of a measurement after digital processing.

To obtain furthermore a smooth recording curve, second data processing means are accomodated. FIG. 4b shows the curve of FIG. 4a when the data have been processed. The curve is then a continuous curve, the terminals $A_2$ and $B_1$, $B_2$ and $C_1$ etc. having been brought to coincidence.

These second data processing means comprise a logic circuit but may optionally be constituted by a wired circuit. When a logic circuit is sued, the following algorith is employed:

---

1) Initialising the measurement of the signal supplied by the proportional counter, i.e. a mV multimeter having a range from 0 to 100 mV.

2) MEASURING
    a) Boundary of the graph
    b) Boundary of the measurement
    c) Filter change test
    $d_1$) If the multimeter measures $>90$ mV $\rightarrow$, the most absorbing filter is placed in position ;
    $d_2$) If the multimeter measurement $<$ bounds of the minimal reflection (for example, 20 or 50 mV)$\rightarrow$, the least absorbing filter is positioned;

3) End of measuremnt
    a) SAVING the file
    b) NORMALISING and correcting the measurements.
    c) STORING a measurement $\rightarrow$ name of the file 4) RETRIEVING the measurements
    $a_1$) linear
    $a_2$) linear-logarithmical.

5) PRINTING: printed output

6) FORMATTING (ASCII) = Converting a file into machine language for use by the main computer.

---

We claim:

1. An X-ray diffractometer device, comprising an X-ray source generating a beam of X-rays, a collimator device for the source, a sample support, a collimator device for the beam reflected by the sample and a counter producing an output signal in the form of a voltage which is proportional to the number of photons reflected by the sample, characterized, in that, it furthermore includes:

a motor drive for the sample support;

means for recording the signal Y supplied by the proportional counter as a function of the angle e between the plane of incident of the sample and the incident beam, denoted X;

mechanical means having a support for a plurality of filters having different absorption coefficients and including a motor drive for this filter support;

data processing means including means for:

measuring the value of the signal Y originating from the proportional counter relative to ranges whose boundaries are predetermined; and if a boundary has been reached, for:

causing a recording interrupt and an interruptor of the sample motor drive to stop;

selecting a filter from the plurality of filters;

causing the start of an interruptor of the filter support motor drive in such a manner as to move the selected filter into the path of the X-ray beam reflected by the sample;

causing the start of the recording interrupt and the interruptor of the sample motor drive.

2. A device as claimed in claim 1, characterized, in that, it furthermore includes said second data processing means for smoothing the recorded curves.

3. A device as claimed in one of the claim 1, characterized, in that, the mechanical means comprise a means for fixing the filter support in the position in which a selected filter is positioned in the path of the beam reflected by the sample.

4. A device as claimed in claim 3, characterized, in that, the fixing means has apertures made in a support coupled to the filter support, in a quantity corresponding to the number of filters, and disposed such that when an aperture passes through the path of a beam in an emitter-receiver diode system the interruptor of the filter motor drive is adjusted to its stop position.

5. A device as claimed in claim 1, characterized, in that, the plurality of filters comprises filters for X-rays whose coefficient of absorption A is chosen from among $10^0, 10^1, \ldots 10^n$ wherein n is an integer, and in that the filters are accomodated on the filter support in a sequence such that their coefficient of absorption A decrease.

6. A device as claimed in claim 5, characterized, in that, the filter support is a plate which is driven by a motor via a belt.

7. A device as claimed in anyone of claim 4, characterized, in that, the apertures are made in a plate which is driven by a motor via a belt.

8. A device as claimed in claim 7, characterized, in that, the filter support and the apertured plate are driven by the same motor.

9. A device as claimed in claim 1, characterized, in that, the filters comprise metal strips with decreasing width e.

10. A device as claimed in claim 9, characterized, in that, the metals for the filters are chosen as a function of the wavelength of the X-ray source from among Cu, Ni, Al.

* * * * *